United States Patent [19]

Kohda et al.

[11] Patent Number: 4,563,454

[45] Date of Patent: Jan. 7, 1986

[54] PROPANONE DERIVATIVES IN ANTIALLERGIC COMPOSITIONS

[76] Inventors: Akihide Kohda, 8-20, 3-chome, Fukumitsu-Higashi, Gifu-shi, Gifu-ken; Teikichi Kurosaki, 6-42, Nishi-Imagawa-cho, Higashi-Sumiyoshi-ku, Osaka-shi, Osaka-fu, both of Japan

[21] Appl. No.: 693,838

[22] Filed: Jan. 24, 1985

Related U.S. Application Data

[60] Continuation of Ser. No. 593,184, Mar. 27, 1984, abandoned, which is a continuation of Ser. No. 494,497, May 18, 1983, abandoned, which is a continuation of Ser. No. 206,565, Nov. 13, 1980, abandoned, which is a division of Ser. No. 79,460, Sep. 27, 1979, Pat. No. 4,277,474, which is a continuation of Ser. No. 13,887, Feb. 22, 1979, abandoned.

[30] Foreign Application Priority Data

Feb. 22, 1978 [JP] Japan .................................. 53-19303

[51] Int. Cl.$^4$ .................. A61K 31/535; A61K 31/445
[52] U.S. Cl. ..................................... 514/239; 514/319; 514/428; 514/656
[58] Field of Search ............... 424/267, 250, 274, 330, 424/248.57, 248.58; 514/319, 428, 239, 656

[56] References Cited

U.S. PATENT DOCUMENTS

2,282,907   5/1942   ter Horst .......................... 546/237 X
3,151,124   9/1964   Huebner .......................... 546/237 X
3,995,047  11/1976   Morita et al. ................... 546/237 X

FOREIGN PATENT DOCUMENTS

2362337   7/1974   Fed. Rep. of Germany .

OTHER PUBLICATIONS

Guette, M., et al., *Bull. Soc. Chim. Fr.,* 1975, (11–12, Pt. 2), 2759–2762.

*Primary Examiner*—Richard A. Schwartz
*Attorney, Agent, or Firm*—Quaintance, Murphy & Presta

[57] ABSTRACT

New propanone derivatives, the pharmacologically allowable salts thereof, their manufacturing process and pharmaceutical composition containing at least one of them as the active ingredient.

15 Claims, 2 Drawing Figures

PROPANONE DERIVATIVES IN ANTIALLERGIC COMPOSITIONS

This is a continuation of Ser. No. 593,187 filed Mar. 27, 1984, abandoned, which was a continuation of Ser. No. 494,497 filed May 18, 1983, abandoned, which was a continuation of Ser. No. 206,565 filed Nov. 13, 1980, abandoned, which was a division of Ser. No. 079,460 filed Sept. 27, 1979 which issued as U.S. Pat. No. 4,277,474, which was a continuation of Ser. No. 013,887 filed Feb. 22, 1979, abandoned.

BACKGROUND OF THE INVENTION

The present invention relates to new propanone derivatives, the pharmacologically allowable salts thereof, their manufacturing process and pharmaceutical composition containing at least one of them as the active ingredient.

It is known that a so-called "chemical mediator", i.e., biochemical substance in a living body such as histamine, serotonin, bradykinin, acetylcholine or SRS-A plays an important role in the appearance of various allergic symptoms in the human body.

Thus something which antagonizes such biochemical substance and/or inhibits its release would be useful for treating allergic diseases and from this standpoint, various compounds have been synthesized and clinically tried so far.

Discovering that a certain propanone derivative exhibits a prominent anti-SRS-A effect, inhibitory effect on histamine release, inhibitory effect on experimental atopic asthma and/or inhibitory effect on homo PCA reaction, the present inventors have accomplished the present invention.

The object of the present invention is to offer new propanone derivatives useful for treating allergic diseases. Another object of the present invention is to offer the manufacturing process of this derivative. Still another object of the present invention is to offer pharmaceutical composition containing at least one of the compounds according to the present invention as the active ingredient and to give directions to use this pharmaceutical composition.

SUMMARY OF THE INVENTION

The compounds according to the present invention include propanone derivative of the general formula (I):

$$A-\overset{O}{\underset{\|}{C}}-\overset{R^1}{\underset{|}{CH}}-CH_2-B \quad (I)$$

wherein A is non-substituted aryl group or aryl group substituted by hydroxyl group, lower alkoxy group or halogen, or non-substituted benzo[b]thienyl group or benzo[b]thienyl group substituted by hydroxyl group, lower alkyl group, lower alkoxy group, aryl group or halogen, B is di-lower alkylamino group or heterocyclic group which contains at least one nitrogen atom and may be substituted by lower alkyl group or aralkyl group; however, when A is p-methylphenyl group, B denotes a group other than piperidino group, and $R^1$ is hydrogen, lower alkyl group or aryl group, and the pharmacologically allowable salts thereof.

As evident from the results of pharmacological tests later to be described, the compounds according to the present invention exhibit a prominent anti-SRS-A effect, inhibitory effect on histamine release, inhibitory effect on experimental atopic asthma and/or inhibitory effect on homo PCA reaction; and accordingly they are useful for treating allergic diseases such as bronchial asthma, allergic rhinitis and allergic dermatitis.

Among the above compounds, pharmacologically preferable compounds are ones expressed by the above-mentioned general formula (I) wherein A is non-substituted phenyl group or phenyl group substituted by more than one, preferably one or two groups; or naphthyl group, tetrahydronaphthyl group, indanyl group or benzo[b]thienyl group non-substituted or substituted by one or two groups; said substituent being one selected from lower alkyl group, lower alkoxy group, aryl group, hydroxyl group and halogen, B is di-lower alkylamino group, or pyrrolidino group, piperidino group, piperazino group or morpholino group non-substituted or substituted by lower alkyl group or aralkyl group, and $R^1$ is hydrogen, methyl, ethyl or phenyl group, and their pharmacologically allowable salts.

Such preferable compounds include specifically; for instance, 2-methyl-3-dimethylamino-1-tolylpropanone, 2-methyl-3-diethylamino-1-tolylpropanone, 2-methyl-3-dipropylamino-1-tolylpropanone, 2-methyl-3-dimethylamino-1-xylylpropanone, 2-methyl-3-pyrrolidino-1-tolylpropanone, 2-methyl-3-(methyl-substituted piperidino)-1-tolylpropanone, 2-methyl-3-piperidino-1-xylylpropanone, 2-methyl-3-(methyl-substituted piperidino)-1-xylylpropanone, 2-methyl-3-(4-methylpiperazino)-1-tolylpropanone, 2-methyl-3-(4-methylpiperazino)-1-xylylpropanone, 2-methyl-3-(4-ethylpiperazino)-1-tolylpropanone, 2-methyl-3-(4-isopropylpiperazino)-1-tolylpropanone, 2-methyl-3-(4-isobutylpiperazino)-1-tolylpropanone, 2-methyl-3-(4-benzylpiperazino)-1-tolylpropanone, 2-methyl-3-(4-ethylpiperazino)-1-(ethyl-substituted phenyl)propanone, 2-methyl-3-(4-ethylpiperazino)-1-(ethyl-methylphenyl)propanone, 2-methyl-3-morpholino-1-tolylpropanone, 2-methyl-3-piperidino-1-(butylphenyl)propanone, 2-methyl-3-piperidino-1-(hexylphenyl)propanone, 2-methyl-3-piperidino-1-(hydroxyphenyl)propanone, 2-methyl-3-piperidino-1-(methoxyphenyl)propanone, 2-methyl-3-piperidino-1-(dimethoxyphenyl)propanone, 2-methyl-3-piperidino-1-(ethoxyphenyl)propanone, 2-methyl-3-piperidino-1-(propoxyphenyl)propanone, 2-methyl-3-piperidino-1-(hydroxy-methoxyphenyl)propanone, 2-methyl-3-piperidino-1-biphenylylpropanone, 2-phenyl-3-piperidino-1-(methoxyphenyl)propanone, 2-methyl-3-dimethylamino-propionaphthone, 2-methyl-3-diethylaminopropionaphthone, 2-methyl-3-dimethylamino-1-(methyl-substituted naphthyl)propanone, 2-methyl-3-pyrrolidino-propionaphthone. 2-methyl-3-(4-methylpiperazino)propionaphthone, 2-methyl-3-piperidino-propionaphthone, 2-methyl-3-(methyl-substituted piperidino)propionaphthone, 2-methyl-3-piperidino-1-(methyl-substituted naphthyl)propanone, 2-methyl-3-piperidino-1-(hydroxy-substituted naphthyl)propanone, 2-methyl-3-piperidino-1-(methoxy-substituted naphthyl)propanone, 2-methyl-3-piperidino-1-(ethyl-methoxy substituted naphthyl)- propanone, 2-methyl-3-piperidino-1-(ethoxy-substituted naphthyl)propanone, 2-methyl-3-morpholino-propionaphthone, 2-methyl-3-piperidino-1-(ethyl-substituted naphthyl)propanone, 2-methyl-3-piperidino-1-(chloro-substituted naphthyl)propanone, 2-methyl-3-piperidino-1-(chloro-methyl-substituted naphthyl)propanone, 2-methyl-3-piperidino-1-(bromo-substituted naphthyl)propanone, 3-piperidinopropionaphthone, 2-methyl-3-piperidino-1-(5,6,7,8-tetrahydronaphthyl)propanone, 2-methyl-3-(methyl-substituted piperidino)-1-(5,6,7,8-tetrahydronaphthyl)propanone, 2-methyl-3-piperidino-1-(methyl-substituted-5,6,7,8-tetrahydronaphthyl)propanone, 2-methyl-3-piperidino-1-(dimethyl-substituted 5,6,7,8-tetrahydronaphthyl)propanone, 2-methyl-3-piperidino-1-benzo[b]thienyl-propanone, 2-methyl-3-(methyl-substituted piperidino)-1-benzo[b]thienylpropanone, 2-methyl-3-piperidino-1-(methyl-substituted-benzo[b]thienyl)propanone, 3-piperidino-1-(dimethyl-substituted phenyl)propanone, 2-methyl-3-piperidino-1-(diethyl-substituted phenyl)propanone, 2-methyl-3-piperidino-1-(propyl-substituted phenyl)propanone, 2-methyl-3-piperidino-1-(trimethyl-substituted phenyl)propanone, 2-methyl-3-piperidino-1-(pentamethyl-substituted phenyl)propanone, 2-methyl-3-piperidino-propiophenone, 2-methyl-3-(benzyl-substituted piperidino)propionaphthone, 2-ethyl-3-piperidinopropionaphthone, 2-methyl-3-piperidino-1-indanylpropanone, 3-piperidino-1-(methoxy-substituted naphthyl)propanone, 3-piperidino-1-(hexyl-substituted phenyl)propanone, 3-piperidino-1-(heptyl-substituted phenyl)propanone, 3-piperidino-1-(octyl-substituted phenyl)propanone, 3-piperidino-1-(decyl-substituted phenyl)propanone, 2-methyl-3-piperidino-1-(heptyl-substituted phenyl)propanone, 2-methyl-3-piperidino-1-(octyl-substituted phenyl)propanone, 2-methyl-3-piperidino-1-(decyl-substituted phenyl)propanone, 2-methyl-3-piperidino-1-(chloro-methoxy-substituted phenyl)propanone, 2-methyl-3-piperidino-1-(dichloro-substituted phenyl)propanone, 2-methyl-3-piperidino-1-(isopropyl-substituted phenyl)propanone, 2-methyl-3-piperidino-1-(isobutyl-substituted phenyl)propanone, 2-methyl-3-piperidino-1-(tert-butyl-substituted phenyl)propanone, 2-methyl-3-dimethylamino-1-(methoxy-substituted naphthyl)propanone, 2-methyl-3-(methyl-substituted piperidino)-1-(methoxy-substituted naphthyl)propanone and 2-phenyl-3-piperidino-1-tolylpropanone; and pharmacologically allowable salts of these compounds.

More preferable compounds are;
2,4'-dimethyl-3-dimethylaminopropiophenone, 2,4'-dimethyl-3-diethylaminopropiophenone, 2,4'-dimethyl-3-morpholinopropiophenone, 2,4'-dimethyl-3-pyrrolidinopropiophenone, 2,4'-dimethyl-3-(4-methylpiperazino)propiophenone, 2,4'-dimethyl-3-(4-ethylpiperazino)propiophenone, 2,4'-dimethyl-3-(4-isobutyl-piperazino)propiophenone, 4'-methoxy-2-methyl-3-piperidinopropiophenone, 4'-ethoxy-2-methyl-3-piperidinopropiophenone, 2-methyl-3-piperidino-β-propionaphthone, 2-methyl-3-dimethylamino-β-propionaphthone, 2-methyl-3-morpholino-β-propionaphthone, 2-methyl-3-pyrrolidino-β-propionaphthone, 2,3',4'-trimethyl-3-piperidinopropiophenone, 3',4'-dimethoxy-2-methyl-3-piperidinopropiophenone, 2,4'-dimethyl-3-(4-benzylpiperazino)propiophenone, 4'-methoxy-2-phenyl-3-piperidinopropiophenone, 4'-hydroxy-2-methyl-3-piperidinopropiophenone, 4'-hydroxy-3'-methoxy-2-methyl-3-piperidinopropiophenone, 2-methyl-3-piperidino-α-propionaphthone, 2-methyl-3-piperidino-4'-phenylpropiophenone, 2-methyl-3-piperidino-1-(benzo[b]thiophene-3'-yl)-propanone-1,4'-hexyl-2-methyl-3-piperidinopropiophenone, 2-methyl-3-piperidino-5',6',7',8'-tetrahydro-2'-propionaphthone, 2-methyl-3-(3'-methylpiperidino)-β-propionaphthone, 2-methyl-3-(4'-methylpiperazino)-β-propionaphthone, 2-methyl-3-(2-methylpiperidino-β-propionaphthone, 2-methyl-3-(4-benzylpiperidino)-β-propionaphthone, 3',4'-dimethyl-3-piperidinopropiophenone, 3-piperidino-β-propionaphthone, 2-ethyl-3-piperidino-β-propionaphthone, 1-(5-indanyl)-2-methyl-3-piperidinopropanone, 3',4'-diethyl-2-methyl-3-piperidinopropiophenone, 2-methyl-3-piperidinopropiophenone, 4'-n-propyl-2-methyl-3-piperidinopropiophenone, 2,2',4',6'-tetramethyl-3-piperidinopropiophenone, 2,2',3',4',5',6'-hexamethyl-3-piperidinopropiophenone, 6'-methoxy-3-piperidino-2'-propionaphthone, 6'-methoxy-2-methyl-3-piperidino-2'-propionaphthone, 4'-n-hexyl-3-piperidinopropiophenone, 4'-n-heptyl-3-piperidinopropiophenone, 4'-n-octyl-3-piperidinopropiophenone, 4'-n-decyl-3-piperidinopropiophenone, 1'-hydroxy-2-methyl-3-piperidino-2'-propionaphthone, 4'-n-heptyl-2-methyl-3-piperidinopropiophenone, 2-methyl-4'-n-octyl-3-piperidinopropiophenone, 4'-n-decyl-2-methyl-3-piperidinopropiophenone, 3'-chloro-4'-methoxy-2-methyl-3-piperidinopropiophenone, 3',4'-dichloro-2-methyl-3-piperidinopropiophenone, 2,6'-dimethyl-3-piperidino-2'-propionaphthone, 6'-hydroxy-2-methyl-3-piperidino-2'-propionaphthone, 6'-chloro-2-methyl-3-piperidino-2'-propionaphthone, 4'-isopropyl-2-methyl-3-piperidinopropiophenone, 4'-n-butyl-2-methyl-3-piperidinopropiophenone, 4'-isobutyl-2-methyl-3-piperidinopropiophenone, 4'-tert-butyl-2-methyl-3-piperidinopropiophenone, 6'-methoxy-2-methyl-3-dimethylamino-2'-propionaphthone, 6'-methoxy-2-methyl-3-(4-methylpiperidino)-2'-propionaphthone and 4'-methyl-2-phenyl-3-piperidinopropiophenone, and pharmacologically allowable salts of these compounds.

The compound according to the present invention can be obtained by reacting a compound expressed by the general formula (II):

wherein A and $R^1$ denote the same meanings as above, with a formaldehyde, and a compound of the general formula (III):

wherein B denotes the same meaning as above, or its salt.

For the above reaction it is preferable to use solvent which produces azeotropic mixture with water, especially a solvent system which separates from water when the azeotropic mixture with water is condensed. Such solvents are, for example, ethanol, benzene, toluene, nitroalkanes or lower esters of lower fatty acid. These are employed singly or as mixed; and the reaction temperature can be controlled to a desired range by appropriately combining them.

The formaldehydes to be used for the above reaction include formaldehyde and its linear or cyclic polymers.

The compounds according to the present invention are yielded in the form of free base or its salt. This salt can be converted in a free base by the known method in the art. Meanwhile this free base can be turned into a pharmacologically allowable salt through contact with an inorganic or organic acid such as hydrochloric acid, sulfuric acid, phosphoric acid, formic acid, lactic acid, tartaric acid, citric acid, etc.

The manufacturing process of the compound according to the present invention is explained in detail by working examples.

EXAMPLE 1

A mixture of 125 ml of nitromethane, 35 ml of toluene, 20 ml of ethanol, and 1 ml of concentrated hydrochloric acid was mixed together with 18.6 g of 4'-methylpropiophenone, 27.0 g of N-isobutylpiperazine dihydrochloride and 8.5 g of trioxane. The mixture was heated with stirring under reflux for 4 hrs. while distilling off water generated through the reaction. After cooling, the reaction mixture was added with ether, and the precipitate was filtered, which was dissolved in water. The solution was adjusted to pH 6 with 5N sodium hydroxide, washed with ether, and further adjusted to pH 7 with 5N sodium hydroxide. The obtained solution was extracted with ether and the extract was dried, and white crystals generated by introducing dry hydrogen chloride were filtered and dried. The product was recrystallized from an ethanol-acetone mixed solvent, yielding 2,4'-dimethyl-3-(4-isobutylpiperazino)-propiophenone dihydrochloride. (yield 46.5%), m.p. 215°–220° C.

| Elementary analysis ($C_{19}H_{30}N_2O.2HCl$) | | | | |
| --- | --- | --- | --- | --- |
| | C % | H % | N % | Cl % |
| Calculated: | 60.79 | 8.59 | 7.46 | 18.89 |
| Found: | 60.54 | 8.65 | 7.60 | 18.80 |

EXAMPLE 2

283 ml of azeotropic solvent (200 ml of nitromethane, 28 ml of ethanol and 55 ml of toluene), 36.8 g of β-propionaphthone, 36.5 g of piperidine hydrochloride, 13.5 g of paraformaldehyde and 1 ml of concentrated hydrochloric acid were mixed and the mixture was heated under reflux for 2 hrs. while distilling off water generated during the reaction. The precipitate obtained after addition of nitromethane and cooling was filtered and dried. Through recrystallization from a mixture of methanol:acetone (1:3) and then from ethanol, 33 g of crystalline powder of 2-methyl-3-piperidino-β-propionaphthone hydrochloride was obtained. (yield 52.0%), m.p. 196°–197° C.

| Elementary analysis ($C_{19}H_{23}NO.HCl$) | | | |
| --- | --- | --- | --- |
| | C % | H % | N % |
| Calculated: | 71.80 | 7.61 | 4.41 |
| Found: | 71.66 | 7.74 | 4.49 |

EXAMPLE 3

A mixture of 200 ml of azeotropic solvent (140 ml of nitromethane, 21 ml of ethanol, and 39 ml of toluene) and 2 ml of concentrated hydrochloric acid was added with 36.0 g of β-propionaphthone, 24.5 g of dimethylamine hydrochloride and 13.5 g of paraformaldehyde and the mixture was heated under reflux for 1.5 hrs. while distilling off water generated through the reaction. After cooling, the solvent was removed from the reaction mixture by distillation under reduced pressure. The residue was dissolved in water. The solution was washed with ether, and adjusted to be alkaline with 5N sodium hydroxide. The alkaline solution was extracted with ether and the ether extract was washed with water and then dried. Next, the crystals yielded by introducing dry hydrogen chloride were filtered and recrystallized from ethanolacetone, yielding 24.0 g of white crystals of 2-methyl-3-dimethylamino-β-propionaphthone hydrochloride. (yield 43.2%), m.p. 160°–161° C.

| Elementary analysis ($C_{16}H_{17}NO.HCl$) | | | | |
| --- | --- | --- | --- | --- |
| | C % | H % | N % | Cl % |
| Calculated: | 69.18 | 7.26 | 5.04 | 12.76 |
| Found: | 69.07 | 7.19 | 5.08 | 12.65 |

EXAMPLE 4

40 g of β-propionaphthone, 12.5 g of paraformaldehyde and 37 g of morpholine hydrochloride were dissolved in 300 ml of azeotropic solvent (210 ml of nitromethane, 30 ml of ethanol and 60 ml of benzene) and added with 1 ml of concentrated hydrochloric acid. The mixture was heated with stirring under reflux for 2 hrs. while distilling off water generated during the reaction. The reaction mixture was concentrated under reduced pressure. The crystals precipitated were washed with ether and filtered. The crystals were suspended in ethanol, heated under reflux, and filtered after cooling to yield crude crystals, which were recrystallized from methanol, yielding 55.3 g of milky white crystalline powder of 2-methyl-3-morpholine-β-propionaphthone hydrochloride. (yield 79.6%), m.p. 182.5°–182.8° C.

| Elementary analysis ($C_{18}H_{21}NO_2.HCl$) | | | | |
| --- | --- | --- | --- | --- |
| | C % | H % | N % | Cl % |
| Calculated: | 67.60 | 6.93 | 4.38 | 11.08 |
| Found: | 67.55 | 6.88 | 4.36 | 10.94 |

EXAMPLE 5

72.0 g of 3',4'-dimethylpropiophenone, 59.4 g of piperidine hydrochloride and 20.0 g of paraformaldehyde, 300 ml of ethyl acetate and 1 ml of concentrated hydrochloric acid were heated with stirring under reflux for 2.5 hours, while distilling off water generated through the reaction. After cooling, crystals precipitated were filtered and recrystallized from a mixture of alcohol-acetone, yielding white crystals of the object product. Each filtrate was collected, concentrated under reduced pressure to dryness, and dissolved in water. The solution was washed with ether, then adjusted to be alkaline with 5N sodium hydroxide and extracted with ether. The extract was washed and then ether was removed after addition of concentrated hydrochloric acid, and the residue was recrystallized from a mixture of alcohol-acetone, yielding white crystals of 2,3',4'-trimethyl-3-piperidinopropiophenone hydrochloride (total yield 61.3%), m.p. 184°–185° C.

| Elementary analysis ($C_{17}H_{25}NO.HCl$) | | | | |
| --- | --- | --- | --- | --- |
| | C % | H % | N % | Cl % |
| Calculated: | 69.02 | 8.86 | 4.73 | 11.98 |

-continued

| Elementary analysis (C$_{17}$H$_{25}$NO.HCl) | | | |
|---|---|---|---|
| | C % | H % | N % | Cl % |
| Found: | 68.81 | 8.60 | 4.88 | 11.90 |

EXAMPLE 6

36.8 g of β-propionaphthone, 13.5 g of paraformaldehyde and 21.5 g of pyrrolidine were dissolved in 285 ml of azeotropic solvent (200 ml of nitromethane, 30 ml of ethanol and 55 ml of toluene) and added with 30 ml of concentrated hydrochloric acid. The mixture was heated under reflux for 2 hrs. while distilling off water generated through the reaction. The reaction mixture was concentrated under reduced pressure and the crystals precipitated were washed with acetone and filtered off. The product was dissolved in water, washed with ether, adjusted to be alkaline with 5N sodium hydroxide, and extracted with ether. The extract was washed with water and dried over anhydrous sodium sulfate, and the crystals yielded by introducing dry hydrogen chloride were filtered. Through recrystallization from alcohol-acetone and water, 10.5 g of crystalline powder of 2-methyl-3-pyrrolidino-β-propionaphthone hydrochloride was obtained (yield 17.3%), m.p. 189°–190° C.

| Elementary analysis (C$_{18}$H$_{21}$NO.HCl) | | | |
|---|---|---|---|
| | C % | H % | N % | Cl % |
| Calculated: | 71.16 | 7.30 | 4.61 | 11.67 |
| Found: | 71.05 | 7.34 | 4.61 | 11.58 |

EXAMPLE 7

A mixture of 210 ml of nitromethane, 32 ml of ethanol, 58 ml of toluene and 2 ml of concentrated hydrochloric acid was added with 38.8 g of 3',4'-dimethoxypropiophenone, 26.8 g of piperidine hydrochloride and 9.0 g of paraformaldehyde. The mixture was heated under reflux for 1.5 hrs. while distilling off water generated through the reaction. The reaction mixture was concentrated under reduced pressure. The crystals precipitated were washed with acetone and filtered. Recrystallization of this product from a mixture of alcohol-acetone gave white crystalline powder of the object compound. The mother liquor of recrystallization was concentrated under reduced pressure to dryness and the residue was dissolved in water. The solution was washed with ether and adjusted to be alkaline with 5N sodium hydroxide, extracted with ether and the ether extract was washed with water and then dried over anhydrous sodium sulfate. The crystals obtained by introducing dry hydrogen chloride were filtered and through recrystallization from a mixture of ethanol-acetone, white crystalline powder of 3',4'-dimethoxy-2-methyl-3-piperidinopropiophenone hydrochloride was obtained. (total yield 32.0%), m.p. 171°–172° C.

| Elementary analysis (C$_{17}$H$_{25}$NO$_3$.HCl) | | | |
|---|---|---|---|
| | C % | H % | N % | Cl % |
| Calculated: | 62.28 | 7.99 | 4.27 | 10.81 |
| Found: | 62.40 | 7.97 | 4.19 | 10.78 |

EXAMPLE 8

A mixture of 125 ml of nitromethane, 20 ml of ethanol, 35 ml of toluene and 2 ml of concentrated hydrochloric acid was added with 22.6 g of p-methoxyphenyl benzyl ketone, 18.2 g of piperidine hydrochloride and 6.9 g of paraformaldehyde. The mixture was heated under reflux for 1.5 hrs. while distilling off water generated through the reaction. After cooling, the solvent was removed from the reaction mixture under reduced pressure. The residue was dissolved in water, and the solution was extracted with ether, then with benzene, and the extract was dried over anhydrous sodium sulfate. Recrystallization of the product from methanol-acetone after removal of the solvent gave 14.5 g of white crystals of 4'-methoxy-2-phenyl-3-piperidinopropiophenone hydrochloride. (yield 40.3%), m.p. 148°–149° C.

| Elementary analysis (C$_{21}$H$_{25}$NO$_2$.HCl) | | | |
|---|---|---|---|
| | C % | H % | N % | Cl % |
| Calculated: | 70.08 | 7.28 | 3.89 | 9.85 |
| Found: | 69.83 | 7.44 | 3.87 | 9.71 |

EXAMPLE 9

A mixture of 140 ml of nitromethane, 40 ml of toluene, 20 ml of ethanol and 2 ml of concentrated hydrochloric acid was mixed with 37.7 g of 6-propionyltetralin, 26.8 g of piperidine hydrochloride and 9.0 g of formaldehyde (used in the form of 40% aqueous formaldehyde). The mixture was heated under reflux for 1 hr. while distilling off water generated during the reaction. After cooling, the crystals precipitated were filtered and recrestallized from a mixture of alcohol-acetone to yield white crystalline powder of the object compound. The filtrate of recrystallization was concentrated under reduced pressure to dryness, and the residue was dissolved in water. The solution was washed with ether, adjusted to be alkaline with 1N sodium hydroxide, and extracted with ether. The extract was washed with water, and dried over anhydrous sodium sulfate. Crystals precipitated by introducing dry hydrogen chloride was filtered. Recrystallization of the product from alcohol-acetone gave white crystalline powder of 2-methyl-3-piperidino-5',6',7',8'-tetrahydro-2'-propionaphthone hydrochloride. (total yield 54.1%), m.p. 175.5°–176.5° C.

| Elementary analysis (C$_{19}$H$_{27}$NO.HCl) | | | |
|---|---|---|---|
| | C % | H % | N % | Cl % |
| Calculated: | 70.90 | 8.77 | 4.35 | 11.01 |
| Found: | 70.74 | 8.92 | 4.39 | 10.95 |

EXAMPLE 10

A mixture of 18.4 g of β-propionaphthone, 14.9 g of 3-methylpiperidine hydrochloride, 4.5 g of paraformaldehyde, 1 ml of hydrochloric acid and 250 ml of ethyl acetate was heated for 2.5 hours under reflux while distilling off water generated during the reaction. After cooling, the crystals precipitated were filtered, and recrystallized from a mixture of alcohol-acetone, yielding 15.2 g of white crystalline powder of 2-methyl-3-(3-methylpiperidino)-β-propionaphthone hydrochloride. (yield 45.8%), m.p. 175.5°–177° C.

| Elementary analysis (C₂₀H₂₅NO·HCl) | | | |
|---|---|---|---|
| | C % | H % | N % | Cl % |
| Calculated: | 72.38 | 7.90 | 4.22 | 10.68 |
| Found: | 71.80 | 7.92 | 4.10 | 10.66 |

EXAMPLES 11-58

According to the substantially same process as described in Examples 1-10, the products as listed in Table 2 were obtained from the starting materials listed in Table 1.

TABLE 1

| Example No. | Starting compounds (II) | Starting compounds (III) |
|---|---|---|
| 11 | 4'-methyl propiophenone | diethylamine hydrochloride |
| 12 | " | morpholine hydrochloride |
| 13 | " | pyrrolidone |
| 14 | " | 1-methylpiperazine dihydrochloride |
| 15 | " | 1-ethylpiperazine dihydrochloride |
| 16 | " | N—benzylpiperazine dihydrochloride |
| 17 | 4'-hydroxypropiophenone | piperidine hydrochloride |
| 18 | 4'-hydroxy-3'-methoxy-propiophenone | " |
| 19 | α-propionaphthone | " |
| 20 | 4'-phenylpropiophenone | " |
| 21 | 1-(benzo[b]thiophene-3'-yl)propanone-1 | " |
| 22 | 4'-hexylpropiophenone | " |
| 23 | β-propionaphthone | 4-methylpiperidine hydrochloride |
| 24 | 4'-methylpropiophenone | dimethylamine hydrochloride |
| 25 | 4'-methoxypropiophenone | piperidine hydrochloride |
| 26 | 4'-ethoxypropiophenone | " |
| 27 | p-tolyl benzyl ketone | " |
| 28 | β-propionaphthone | 2-methylpiperidine hydrochloride |
| 29 | " | 4-benzylpiperidine hydrochloride |
| 30 | 3',4'-dimethylacetophenone | piperidine hydrochloride |
| 31 | β-acetonaphthone | piperidine hydrochloride |
| 32 | β-butyronaphthone | " |
| 33 | 5-propionylindane | " |
| 34 | 3',4'-diethylpropiophenone | " |
| 35 | propiophenone | piperidine hydchloride |
| 36 | 4'n-propyl-propiophenone | " |
| 37 | 2',4',6'-trimethyl-propiophenone | " |
| 38 | 2',3',4',5',6'-pentamethyl-propiophenone | " |
| 39 | 6'-methoxy-2'-acetonephthone | " |
| 40 | 6'-methoxy-2'-propionaphthone | " |
| 41 | 4'-n-hexylacetophenone | " |
| 42 | 4'-n-heptylacetophenone | " |
| 43 | 4'-n-octylacetophenone | " |
| 44 | 4'-n-decylacetophenone | " |
| 45 | 1'-hydroxy-2'-propionaphthone | " |
| 46 | 4'-n-heptylpropiophenone | " |
| 47 | 4'-n-octylpropiophenone | " |
| 48 | 4'-n-decylpropiophenone | " |
| 49 | 3'-chloro-4'-methoxypropiophenone | " |
| 50 | 3',4'-dichloropropiophenone | " |
| 51 | 6'-methyl-2'-proplonaphthone | " |
| 52 | 6'-chloro-2'-propionaphthone | " |
| 53 | 4'-isopropylpropiophenone | " |
| 54 | 4'-n-butylpropiophenone | " |
| 55 | 4'-isobutylpropiophenone | " |
| 56 | 4'-tert-butylpropiophenone | " |
| 57 | 6'-methoxy-2'-propionaphthone | dimethylamine hydrochloride |
| 58 | " | 4-methylpiperidine hydrochloride |

TABLE 2

| Example No. | Product (I) | Melting Point (°C.) (Solvent for recrystallization)* | Elementary analysis (%)** | | | |
|---|---|---|---|---|---|---|
| | | | C | H | N | Cl |
| 11 | 2,4'-dimethyl-3-diethylamino-propiophenone hydrochloride | 88.0–89.0 | 62.60<br>62.88 | 9.11<br>9.40 | 4.87<br>5.16 | 13.14<br>13.02 |
| 12 | 2,4'-dimethyl-3-morpholino-propiophenone hydrochloride | 155.0–155.5<br>(MEK—EtOH) | 63.48<br>63.22 | 7.82<br>7.92 | 4.94<br>5.02 | 12.49<br>12.50 |
| 13 | 2,4'-dimethyl-3-pyrrolidino-propiophenone hydrochloride | 156.0–157.0<br>(acetone) | 67.28<br>67.45 | 8.28<br>8.50 | 5.23<br>5.42 | 13.24<br>13.08 |
| 14 | 2,4'-dimethyl-3-(4-methylpiperazino)-propiophenone dihydrochloride | 190.0–193.0<br>(MtOH—acetone) | 56.69<br>56.66 | 7.83<br>7.92 | 8.26<br>8.29 | 20.92<br>21.84 |
| 15 | 2,4'-dimethyl-3-(4-ethylpiperazino)-propiophenone dihydrochloride | 178.0–179.0<br>(EtOH—acetone) | 58.79<br>58.77 | 8.13<br>8.16 | 8.06<br>7.94 | 20.41<br>20.23 |
| 16 | 2,4'-dimethyl-3-(4-benzylpeperazino)-propiophenone dihydrochloride | 217.0–245 (Dec.)<br>(MtOH) | 64.54<br>64.34 | 7.39<br>7.47 | 6.84<br>6.91 | 17.32<br>17.53 |
| 17 | 4'-hydroxy-2-methyl-3-piperidino-propiophenone hydrochloride | 197.0–198.0<br>(EtOH—acetone) | 63.48<br>63.25 | 7.81<br>7.95 | 4.94<br>5.06 | 12.49<br>12.37 |
| 18 | 4'-hydroxy-3'-methoxy-2-methyl-3-piperidinopropiophenone hydrochloride | 156.0–157.0<br>(EtOH—acetone) | 61.24<br>61.34 | 7.71<br>7.73 | 4.46<br>4.38 | 11.30<br>11.25 |
| 19 | 2-methyl-3-piperidino-α-propionaphthone hydrochloride | 165.0–166.0<br>(H$_2$O—acetone) | 71.80<br>71.67 | 7.61<br>7.81 | 4.41<br>4.38 | 11.15<br>11.04 |
| 20 | 2-methyl-3-piperidino-4'-phenyl-propiophenone hydrochloride | 174.5–175.5<br>(EtOH—acetone) | 73.35<br>73.61 | 7.62<br>7.57 | 4.07<br>4.19 | 10.31<br>10.26 |
| 21 | 2-methyl-3-piperidino-1-(benzo[b]thio-phene-3-yl)propanone-1 hydrochloride | 164.0–165.0<br>(methyl isobutyl ketone) | 63.04<br>62.77 | 6.85<br>6.91 | 4.32<br>4.42 | 10.95<br>10.83 |
| 22 | 4'-hexyl-2-methyl-3-piperidinopropio-phenone hydrochloride | 157.5–158.5<br>(EtOH—acetone) | 71.66<br>71.57 | 9.74<br>9.68 | 3.95<br>3.81 | 10.07<br>10.01 |
| 23 | 2-methyl-3-(4-methylpiperidino)-β-propionaphthone hydrochloride | 187–188<br>(alcohol-acetone) | 72.38<br>72.20 | 7.90<br>7.78 | 4.22<br>4.18 | 10.68<br>10.71 |
| 24 | 2,4'-dimethyl-3-dimethylamino-propiophenone hydrochloride | 145.0–146.0<br>(MEK—EtOH) | 64.70<br>63.56 | 8.34<br>8.31 | 5.79<br>5.82 | 14.66<br>14.55 |
| 25 | 4'methoxy-2-methyl-3-piperidino-propiophenone hydrochloride | 168.0–168.5<br>(MEK—EtOH) | 64.53<br>64.25 | 8.12<br>8.15 | 4.72<br>4.66 | 11.90<br>11.91 |
| 26 | 4'-ethoxy-2-methyl-3-piperidinopropio-phenone hydrochloride | 164.0–165.0<br>(isopropanol) | 65.48<br>65.59 | 8.48<br>8.61 | 4.49<br>4.52 | 11.34<br>11.44 |
| 27 | 4'-methyl-2-phenyl-3-piperidino-propiophenone hydrochloride | 162.0–162.5<br>(MtOH—acetone) | 73.35<br>73.20 | 7.62<br>7.71 | 4.07<br>4.02 | 10.31<br>10.27 |
| 28 | 2-methyl-3-(2-methylpiperidino)-β-propionaphthone hydrochloride | 135.5–136.5<br>(MEK—ether) | 72.38<br>72.29 | 7.90<br>7.84 | 4.22<br>4.20 | 10.68<br>10.66 |
| 29 | 2-methyl-3-(4-benzylpiperidino)-β-propionaphthone hydrochloride | 171–172<br>(alcohol-acetone-ether) | 76.54<br>76.86 | 7.41<br>7.86 | 3.43<br>3.62 | 8.69<br>8.66 |
| 30 | 3',4'-dimethyl-3-piperidino-propiophenone hydrochloride | 182–183<br>(alcohol-ether) | 68.19<br>68.34 | 8.58<br>8.67 | 4.97<br>5.07 | 12.58<br>12.54 |
| 31 | 3-piperidino-β-propionaphthone hydrochloride | 191–192<br>(MtOH—ether) | 71.16<br>70.68 | 7.30<br>7.86 | 4.61<br>4.62 | 11.67<br>11.56 |
| 32 | 2-ethyl-3-piperidino-β-propionaphthone hydrochloride | 176–177<br>(alcohol-acetone-ether) | 72.38<br>72.30 | 7.90<br>7.92 | 4.22<br>4.18 | 10.68<br>10.57 |
| 33 | 1-(5-indanyl)-2-methyl-3-piperidinopropanone hydrochloride | 187–188<br>(alcohol-acetone) | 70.23<br>70.37 | 8.51<br>8.71 | 4.55<br>4.54 | 11.52<br>11.59 |
| 34 | 3',4'-diethyl-2-methyl-3-piperidino-propiophenone hydrochloride | 157–158<br>(alcohol-acetone-ether) | 70.46<br>70.60 | 9.34<br>9.18 | 4.32<br>4.30 | 10.95<br>10.38 |
| 35 | 2-methyl-3-piperidinopropiophenone) hydrochloride | 178–179<br>(alcohol-acetone) | 67.28<br>67.46 | 8.28<br>8.20 | 5.23<br>5.18 | 13.24<br>13.19 |
| 36 | 4'-h-propyl-2-methyl-3-piperidino-propiophenone hydrochloride | 169–170<br>(alcohol-acetone-ether) | 69.77<br>69.99 | 9.11<br>9.04 | 4.52<br>4.55 | 11.44<br>11.44 |
| 37 | 2,2',4',6'-tetramethyl-3-piperidinopropiophenone hydrochloride | 133–135<br>(alcohol-acetone-ether) | 69.77<br>69.83 | 9.11<br>9.15 | 4.52<br>4.57 | 11.44<br>11.35 |
| 38 | 2,2',3',4',5',6'-hexamethyl-3-piperi-dinopropiophenone hydrochloride | 220–223<br>(alcohol-ether) | 71.09<br>70.91 | 9.54<br>9.57 | 4.14<br>4.13 | 10.49<br>10.48 |
| 39 | 6'-methoxy-3-piperidino-2'-propionaphthone hydrochloride | 190.5–192.0<br>(MtOH) | 68.35<br>68.19 | 7.25<br>7.22 | 4.20<br>4.31 | 10.62<br>10.58 |
| 40 | 6'-methoxy-2-methyl-3-piperidino-2'-propio-naphthone hydrochloride | 185.5–186.0<br>(MtOH) | 69.05<br>69.00 | 7.53<br>7.46 | 4.03<br>4.20 | 10.19<br>10.02 |
| 41 | 4'-n-hexyl-3-piperidino-propiophenone hydrochloride | 159<br>(acetone) | 71.08<br>71.05 | 9.54<br>9.55 | 4.14<br>4.08 | 10.49<br>10.55 |
| 42 | 4'-n-hexyl-3-piperidino-propiophenone hydrochloride | 154<br>(acetone) | 71.66<br>71.61 | 9.74<br>9.67 | 3.98<br>4.05 | 10.07<br>10.10 |
| 43 | 4'-n-octyl-3-piperidino-propiophenone hydrochloride | 157<br>(acetone) | 72.20<br>72.11 | 9.92<br>9.86 | 3.83<br>3.93 | 9.69<br>9.85 |
| 44 | 4'-n-decyl-3-piperidino-propiophenone hydro- | 151<br>(acetone) | 73.16<br>73.23 | 10.23<br>10.20 | 3.55<br>3.59 | 9.00<br>8.98 |

TABLE 2-continued

| Example No. | Product (I) | Melting Point (°C.) (Solvent for recrystallization)* | Elementary analysis (%)** C | H | N | Cl |
|---|---|---|---|---|---|---|
| 45 | 1'-hydroxy-2-methyl-3-piperidino-2'-propionaphthone hydrochloride | 96–97.5 (MtOH) | 68.35 / 68.09 | 7.25 / 7.16 | 4.20 / 4.35 | 10.62 / 10.53 |
| 46 | 4'-n-heptyl-2-methyl-3-piperidinopropiophenone hydrochloride | 152.5–153.5 (acetone) | 72.20 / 72.18 | 9.92 / 9.95 | 3.83 / 4.00 | 9.69 / 9.74 |
| 47 | 2-methyl-4'-n-octyl-3-piperidinopropiophenone hydrochloride | 148–149.5 (acetone) | 72.69 / 72.73 | 10.08 / 10.32 | 3.69 / 3.60 | 9.33 / 9.32 |
| 48 | 4'-n-decyl-2-methyl-3-piperidinopropiophenone hydrochloride | 143.5–144.5 (acetone) | 73.58 / 73.79 | 10.37 / 10.25 | 3.43 / 3.40 | 8.69 / 8.63 |
| 49 | 3'-chloro-4'-methoxy-2-methyl-3-piperidinopropiophenone hydrochloride | 161.5–162.5 (EtOH—acetone) | 57.84 / 57.90 | 6.98 / 7.01 | 4.22 / 4.08 | 21.34 / 21.38 |
| 50 | 3',4'-dichloro-2-methyl-3-piperidinopropiophenone hydrochloride | 176.0 (acetone) | 53.51 / 53.67 | 5.99 / 5.98 | 4.16 / 4.11 | 31.59 / 31.38 |
| 51 | 2.6'-dimethyl-3-piperidino-2'-propionaphthone hydrochloride | 194.0–194.5 (Dec.) (EtOH) | 72.38 / 72.51 | 7.90 / 7.83 | 4.22 / 4.21 | 10.68 / 10.69 |
| 52 | 6'-chloro-2-methyl-3-piperidino-2'-propionaphthone hydrochloride | 201–202 (Dec.) (MtOH) | 64.78 / 64.87 | 6.58 / 6.69 | 3.98 / 4.09 | 20.13 / 20.09 |
| 53 | 4'-isopropyl-2-methyl-3-piperidinopropiophenone hydrochloride | 181–182 (acetone) | 69.77 / 69.83 | 9.11 / 9.21 | 4.52 / 4.61 | 11.44 / 11.36 |
| 54 | 4'-n-butyl-2-methyl-3-piperidinopropiophenone hydrochloride | 161–162 (acetone) | 70.45 / 70.57 | 9.34 / 9.25 | 4.32 / 4.33 | 10.95 / 10.98 |
| 55 | 4'-isobutyl-2-methyl-3-piperidinopropiophenone hydrochloride | 172–173 (acetone) | 70.45 / 70.71 | 9.34 / 9.31 | 4.32 / 4.45 | 10.95 / 10.96 |
| 56 | 4'-tert-butyl-2-methyl-3-piperidinopropiophenone hydrochloride | 168–169 (acetone) | 70.45 / 70.56 | 9.34 / 9.36 | 4.32 / 4.25 | 10.95 / 10.92 |
| 57 | 6'-methyoxy-2-methyl-3-dimethylamino-2'-propionaphthone hydrochloride | 177.5–178.5 (EtOH—acetone) | 66.33 / 66.45 | 7.20 / 7.12 | 4.55 / 4.61 | 11.52 / 11.48 |
| 58 | 6'-methoxy-2-methyl-3-(4-methylpiperidino)-2'-propionaphthone hydrochloride | 191.5–193.5 (Dec.) (EtOH—acetone) | 69.69 / 69.80 | 7.80 / 7.65 | 3.87 / 3.83 | 9.80 / 9.70 |

*MEK: methyl ethyl ketone, MtOH: methanol, EtOH: ethanol
**upper figure: Calculated value
lower figure: Found value The present invention intends also to produce the compounds having hydroxy group other than those in the Table by dealkylating, dearalkylating or hydrolyzing the compounds having alkoxy group, aralkyloxy group or acyloxy group at aryl moiety respectively, by means of the process publicly known in itself. Namely, this process is especially recommended in such a case that it is hard to produce the compounds according to the present invention directly from hydroxy substituted arylketones.

The following is a concrete example of this process.

EXAMPLE 59

A mixture of 3.3 g of 6'-benzyloxy-2-methyl-3-piperidino-2'-propionaphthone hydrochloride, 5 ml of concentrated hydrochloric acid and 40 ml of acetic acid was agitated under heating at 90° C. for 6 hours. Aqueous solution of sodium bicarbonate was added thereto, and the mixture was extracted with ether-ethyl acetate (2:1). After washing with water, 1% hydrochloric acid was added to move the object product to aqueous phase. It was washed with ether-ethyl acetate and made to be alkaline by aqueous solution of sodium bicarbonate, and then extracted by ether. After washing with water and drying, purification by silica gel column chromatography and active carbon treatment were conducted. Crystals obtained by concentrating under reduced pressure were recrystallized from ethanol-ether, thus producing 1.0 g of 6'-hydroxy-2-methyl-3-piperidino-2'-propionaphthone hydrochloride of light-brown crystals. m.p. 188°–189° C.

| Elementary analysis ($C_{19}H_{23}NO_2 \cdot HCl$) | | | |
|---|---|---|---|
| | C % | H % | N % | Cl % |
| Calculated: | 68.35 | 7.25 | 4.20 | 10.62 |
| Found: | 68.50 | 7.33 | 4.18 | 10.56 |

The following results of toxic and pharmacological tests prove the activity, particularly the antiallergic activity, of the compounds according to the present invention.

Thus the present invention relates to pharmaceutical compositions containing as the active ingredient the compounds expressed by the formula (I) or the pharmacologically allowable salts thereof.

ACUTE TOXICITY

Acute toxicity tests were carried out by intraperitoneal or peroral administration of the compound according to the present invention to groups of 10 ICR-strain male mice (weighing 20 g on the average), and each $LD_{50}$ value was determined by Litchfield-Wilcoxon Method.

As the result it was found that the compounds according to the present invention showed the following values of $LD_{50}$: for instance, 2methyl-3-piperidino-β-propionaphthone hydrochloride, 120 mg/kg when administered intraperitoneally, 370 mg/kg when administered perorally; 2-methyl-3-morpholino-β-propionaphthone hydrochloride, 190 mg/kg when administered intraperitoneally, 540 mg/kg when administered perorally; 2,3′,4′-trimethyl-3-piperidinopropiophenone hydrochloride, 117 mg/kg when administered intraperitoneally, 325 mg/kg when administered perorally; the other compounds exhibiting about the same values of $LD_{50}$.

PHARMACOLOGICAL TESTS (1) Anti-SRS-A effect

The anti-SRS-A effect of the compounds according to the present invention on guinea pig's ileum was measured by Magnus method.

Isolated ileum of the guinea pig was suspended in a Magnus tube which was kept at a temperature of 31±1° C., and after eliminating the effeect of histamine by pretreatment with mepyramine, test compound was administered at a dosage of $10^{-8}$–$10^{-4}$ g/ml. One minute thereafter, the ileum contraction inhibiting rate (%) was measured with use of 1 ml of 80% ethanol solution of SRS-A (150 mg/ml). Representative results are summarized in Table 3.

TABLE 3

| Example No. | Concentration of test compound (g/ml) | | |
|---|---|---|---|
| | $10^{-6}$ | $10^{-5}$ | $10^{-4}$ |
| 1 | 0 ± 0 | 6.7 ± 3.33 | 64.7 ± 7.51 |
| 2 | 10.0 ± 8.08 | 53.7 ± 8.68 | 76.0 ± 7.23 |
| 3 | 1.3 ± 0.88 | 47.0 ± 9.50 | 91.3 ± 3.84 |
| 4 | 13.0 ± 12.50 | 36.3 ± 14.19 | 96.7 ± 3.33 |
| 5 | 12.3 ± 8.25 | 67.7. ± 8.11 | 100.0 ± 0 |
| 6 | 0.3 ± 0.33 | 63.0 ± 6.66 | |
| 7 | 1.0 ± 1.00 | 8.3 ± 2.85 | 85.7 ± 0.67 |
| 11 | 3.0 ± 3.00 | 0.3 ± 0.33 | 68.0 ± 13.05 |
| 12 | 8.3 ± 6.89 | 20.7 ± 5.61 | 69.7 ± 12.13 |
| 13 | 1.3 ± 1.33 | 2.7 ± 2.67 | 80.7 ± 6.98 |

TABLE 3-continued

| Example No. | Concentration of test compound (g/ml) | | |
|---|---|---|---|
| | $10^{-6}$ | $10^{-5}$ | $10^{-4}$ |
| 14 | 10.3 ± 7.98 | 10.3 ± 7.88 | 58.0 ± 4.36 |
| 15 | 0.3 ± 0.33 | 20.7 ± 6.12 | 69.7 ± 3.71 |
| 24 | 4.3 ± 2.40 | 7.7 ± 3.67 | 57.3 ± 5.17 |
| 25 | 6.7 ± 6.67 | 15.0 ± 14.50 | 80.3 ± 7.22 |
| 26 | 6.7 ± 5.24 | 12.3 ± 6.69 | 86.7 ± 3.84 |

(2) Inhibitory effect on histamine release

The inhibitory effect on histamine release of the compounds according to the present invention was investigated as follows.

Peritoneal cavity cells of 6–8 weeks old Wistar-strain male rats were sensitized by incubation at 37° C. for 2 hours in a rat anti-ovalbumin serum (prepared according to the method of Goose et al. [J. Goose, Immunology 16, 749, 1969]). These cells were suspended in a phosphoric acid buffer solution (containing 0.1% of gelatin) and each 0.5 ml portion of this suspension was taken in a polyethylene tube. 1 ml each of solutions of various concentrations of test compound and 0.5 ml of 200 μg/ml of ovalbumin solution were added therein. They were incubated for 20 minutes at 37° C. to measure the histamine release rate. The amount of histamine was measured by a modified Shore method using fluorescence.

Figure 1:
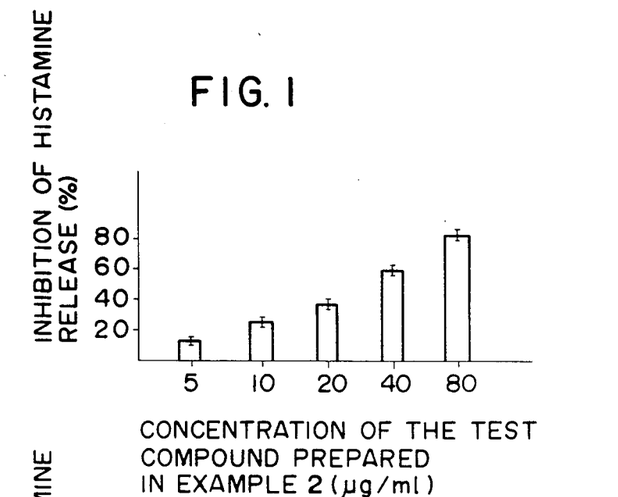
FIGS. 1 and 2 are diagrams illustrating the relation between the concentration of compounds according to the present invention and the inhibitory effect on histamine release.
Figure 2:
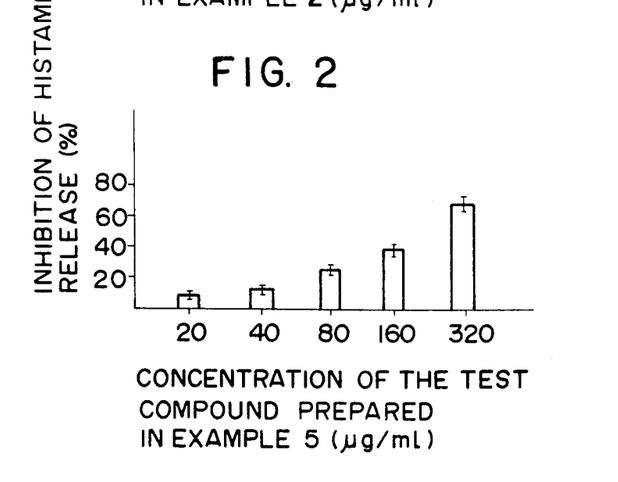

As comparisons, 2,4′-dimethyl-3-piperidinopropiophenone and disodium chromoglicate (DSCG) were employed. Representative results are summarized in Tables 4–7, and FIGS. 1 and 2.

TABLE 4

| Test Compound (Example No.) | Fluorescence intensity (%) | | | Release rate (%) | Net** release rate (%) | Inhibitory effect (%) |
|---|---|---|---|---|---|---|
| | Released histamine | Residual histamine | Total histamine | | | |
| Control | 220 | 252 | 472 | 46.6 | 32.7 | — |
| 2,4′-dimethyl-3-piperidinopropiophenone* | 246 | 238 | 484 | 50.8 | 36.9 | 0 |
| (2)* | 184 | 292 | 476 | 38.6 | 24.7 | 24.5 |
| (4)* | 212 | 268 | 480 | 44.2 | 30.3 | 7.4 |
| (5)* | 210 | 280 | 490 | 42.9 | 29.0 | 11.3 |
| DSCG* | 182 | 312 | 494 | 36.8 | 22.9 | 30.0 |

*Concentration of test compound: 0.01 mM
**Net release rate is calculated by deducting histamine release rate of sensitized peritoneal cavity cells which is not caused by antigen-antibody reaction from the above release rate.

TABLE 5

| Test compound (Example No.) | Concentration of Test compound (mM) | Inhibitory effect on histamine release (%)* |
|---|---|---|
| (10) | 0.05 | 18.0 ± 5.4 |
| (22) | " | 82.0 ± 1.7 |
| (23) | " | 21.4 ± 2.4 |
| (28) | " | 18.5 ± 6.5 |
| (29) | " | 61.0 ± 3.6 |
| (30) | " | 19.4 ± 7.8 |
| (31) | " | 53.4 ± 9.1 |
| (32) | " | 27.2 ± 8.1 |
| (33) | " | 14.4 ± 2.6 |
| (34) | " | 29.1 ± 7.5 |
| (36) | " | 23.6 ± 7.7 |
| DSCG | " | 29.0 ± 6.1 |

*Average value ± S.E. of 3 or 4 times experiments.

TABLE 6

| Test compound (Example No.) | Concentration of Test compound (mM) | Inhibitory effect on histamine release (%) |
|---|---|---|
| 2 | 0.1 | 60 |
| 6 | " | 48 |
| 9 | " | 33.7 |
| 10 | " | 49.9 |
| 22 | " | 87.2 |
| 23 | " | 65.8 |
| 28 | " | 40.7 |
| 29 | " | 98.7 |
| 30 | " | 50.3 |
| 31 | " | 89.6 |
| 32 | " | 42.0 |
| 39 | " | 85 |
| 40 | " | 84 |
| 49 | " | 38 |
| 50 | " | 73 |
| 51 | " | 37 |
| DSCG | " | 70 |

TABLE 7

| Test compound (Example No.) | Concentration of Test compound (mM) | Inhibitory effect on histamine release (%) |
|---|---|---|
| 16 | 0.2 | 72.4 |
| 18 | " | 83.7 |
| 19 | " | 100 |
| 27 | " | 78.5 |

As seen from the above results, the compounds according to the present invention exhibit prominent anti-SRS-A effect and inhibitory effect on histamine release, and their effects depend on the dose.

(3) Experimental atopic asthma

Anti-benzylpenicilloyl bovine γ-globulin serum (anti-$(BPO)_{63}$-BGG serum) of 2048 titer in 7-day homologous PCA which had been obtained by the method of Levine et al. [Levine, B. B. et al., J. Immunol., 106, 29(1971)] was injected at a dosage of 0.25 ml/guinea pig into the hearts of groups of Hartley-strain male guinea pig (a group consisting of four), each weighing 250–300 g, to make them passively sensitive. Forty-eight hours thereafter, the tracheal muscle is cut open under urethane anesthesia and is connected with transducer (MFP-IT and MP-24T of Nihon Kohden Kogyo Co., Ltd.), and the velocity and volume of breathing were measured simultaneously by a multi-purpose monitor-recorder (RM-150 of Nihon Kohden Kogyo Co., Ltd.). The rate of breathing and the ratio of expiration time to inspiration time were calculated from the velocity of breathing. As an antigen to induce the reaction 200 μg/kg of benzylpenicilloyl bovine serum albumin [$(BPO)_{23}$-BSA] obtained by the method of Levine et al. [Levine et al.; J. Clin. Invest., 47, 556 (1968)] was injected through a carnula into the jugular vein.

Compounds according to the present invention and 2,4'-dimethyl-3-piperidinopropiophenone were perorally administered at a dosage of 50 mg/kg, one hour in advance of reaction induction, the results being summarized in Table 8.

TABLE 8

| Measured time (min.) | Rate of breathing (%) | Volume of breathing (%) | Expiration/ inspiration (%) | Rate of breathing (%) | Volume of breathing (%) | Expiration/ inspiration (%) |
|---|---|---|---|---|---|---|
| | Control | | | 2,4'-dimethyl-3-piperidinopropiophenone | | |
| Before test | 100.0 ± 0.00 | 100.0 ± 0.00 | 100.0 ± 0.00 | 100.0 ± 0.00 | 100.0 ± 0.00 | 100.0 ± 0.00 |
| 1 | 141.7 ± 16.21 | 119.8 ± 8.45 | 73.8 ± 5.53 | 120.6 ± 4.98 | 123.4 ± 6.52 | 90.2 ± 4.02 |
| 3 | 90.0 ± 5.58 | 75.5 ± 5.86 | 120.1 ± 9.46 | 98.6 ± 6.55 | 92.6 ± 8.29 | 93.9 ± 5.09 |
| 6 | 75.5 ± 2.41 | 76.2 ± 6.49 | 117.9 ± 7.37 | 89.5 ± 3.36 | 96.7 ± 3.97 | 94.3 ± 5.34 |
| 18 | 78.9 ± 1.56 | 79.7 ± 6.73 | 124.8 ± 6.21 | 91.3 ± 1.57 | 90.6 ± 1.52 | 96.6 ± 2.39 |
| 30 | 75.0 ± 2.62 | 77.6 ± 1.43 | 121.9 ± 6.17 | 93.3 ± 2.80 | 91.4 ± 6.20 | 94.8 ± 4.76 |
| 60 | 75.1 ± 4.46 | 73.1 ± 4.08 | 125.2 ± 6.74 | 86.9 ± 6.14 | 90.9 ± 4.47 | 93.9 ± 3.98 |
| 90 | 79.2 ± 4.56 | 87.0 ± 1.00 | 122.7 ± 1.32 | 84.6 ± 6.03 | 91.0 ± 3.34 | 104.3 ± 6.02 |
| 130 | 73.8 ± 4.29 | 77.0 ± 3.96 | 134.5 ± 5.00 | 87.3 ± 4.44 | 94.9 ± 4.71 | 107.0 ± 3.44 |
| 180 | 81.1 ± 1.34 | 84.9 ± 3.17 | 123.1 ± 4.46 | 87.5 ± 6.43 | 93.8 ± 6.49 | 109.3 ± 6.26 |
| | Example 2 | | | Example 5 | | |
| Before test | 100.0 ± 0.00 | 100.0 ± 0.00 | 100.0 ± 0.00 | 100.0 ± 0.00 | 100.0 ± 0.00 | 100. ± 0.00 |
| 1 | 120.8 ± 3.19 | 108.2 ± 1.78 | 78.4 ± 9.00 | 122.0 ± 16.99 | 100.5 ± 5.01 | 77.6 ± 3.68 |
| 3 | 90.3 ± 3.36 | 86.7 ± 4.14 | 108.7 ± 11.36 | 93.7 ± 7.20 | 86.9 ± 5.99 | 92.3 ± 2.19 |
| 6 | 92.2 ± 5.69 | 90.3 ± 8.26 | 99.8 ± 4.30 | 93.7 ± 5.80 | 86.4 ± 6.96 | 98.7 ± 3.93 |
| 18 | 91.6 ± 5.71 | 86.0 ± 8.49 | 106.5 ± 5.25 | 99.9 ± 4.00 | 86.3 ± 3.71 | 97.7 ± 2.62 |
| 30 | 96.4 ± 4.09 | 93.7 ± 3.75 | 100.3 ± 3.41 | 92.5 ± 1.76 | 86.6 ± 2.44 | 103.2 ± 1.10 |
| 60 | 96.2 ± 3.62 | 96.6 ± 4.92 | 97.0 ± 3.47 | 97.0 ± 1.81 | 93.5 ± 6.17 | 94.3 ± 3.87 |
| 90 | 94.0 ± 5.23 | 97.6 ± 7.12 | 96.5 ± 3.18 | 90.7 ± 6.14 | 93.5 ± 3.78 | 96.7 ± 4.58 |
| 130 | 94.3 ± 6.97 | 92.1 ± 9.25 | 106.4 ± 4.19 | 92.9 ± 5.33 | 87.4 ± 3.03 | 106.2 ± 5.28 |
| 180 | 98.2 ± 5.42 | 97.8 ± 7.28 | 108.7 ± 6.81 | 97.5 ± 1.82 | 95.1 ± 3.33 | 100.1 ± 2.03 |

In this experiment the control group exhibited such a pattern of expiratory dyspnea as encountered in a fit of a human asthma; i.e. immediately after the reaction induced, the rate and volume of breathing transiently increased, followed by a steady decrease, and 3 minutes after the reaction induced, the ratio of expiration/inspiration increased. By contrast, the animals administered with the compounds according to the present invention strongly exhibited the inhibition on the variation from the normal values exhibited in the control group, while the animals administered with 2,4'-dimethyl-3-piperidinopropiophenone showed the less inhibitory effect than the compounds according to the present invention.

The compounds in Examples 2 and 5 were administered to rats to investigate inhibitory effect on homo PCA reaction. The results showed that 5 mg/Kg of intravenous administration of the former could inhibit 62.1% of the reaction and 200 mg/Kg of peroral administration of the latter could inhibit about 70% of the reaction (about 40% in the case of peroral administration of the comparative compound, i.e. 2,4'-dimethyl-3- piperidinopropiophenone); and their effects depended on the dose.

The compounds according to the present invention are useful as anti-allergic agent for treatment of bronchial asthma, allergic rhinitis and allergic dermatitis. They can be administered singly or as combined, in appropriate forms of solid or liquid such as tablet, capsule, powder, ointment, aerosol, solution, suspension or emulsion. They are perorally administered as tablet, capsule, powder or aqueous solution, or non-perorally administered as injection for subcutaneous, intravenous, intramuscular, intrarectal or intranasal, as liquid for dispersion or aerosol in the form of liquid or dry powder for application to the mucosa of nose, throat or trachea, or as ointment.

For solid administration, tablet or capsule may be prepared by combination of the compounds of the present invention with vehicle such as luctose, mannite, corn starch, potato starch and other common additives; the binder such as crystalline cellulose, cellulose derivatives, gum arabic, corn starch and gelatine, the disintegrator such as corn starch, potato starch and carboxymethyl cellulose calcium and the lubricant such as talc and magnesium stearate; or they can be prepared as ointment in combination with the ointment base.

The compounds according to the present invention may also be prepared as an injectable solution or an injectable suspension together with a physiologically acceptable diluent, with or without adding a surface-active agent and other pharmaceutically acceptable assistants. Usually, distilled water for injection, physiological saline solution, aqueous solution of dextrose, vegetable oil for injection and glycols such as propylene glycol, polyethylene glycol are preferable liquid diluents.

For aerosol administration, the compounds according to the present invention are charged into an aerosol vessel in the form of liquid or fine particles, together with gaseous or liquid propellant, and, if desired, together with common assistants such as the wetting agent or the dispersing agent. They may be prepared as a non-pressurized type such as the nebulizer or the atomizer.

The preferable dosage of the compounds according to the present invention depends on patient's condition and the manner of administration. Generally speaking, peroral administration of 0.1–100 mg level of the compound per day per one kg of the patient's body weight would be desirable for the purpose of achieving the expected effect. In the general case of an adult a daily administration of 1 to 10 units of a preparation containing 5–500 mg of the compound according to the present invention will suffice. Non-peroral daily administration, for example, injection, of about $\frac{1}{2}$–1/10 of the above dosage will have approximately the same effect. Daily administration of 1 to 10 units of a preparation containing 0.5–170 mg of the compound according to the present invention is preferred.

Several prescription examples of pharmaceutical compositions containing a compound according to the present invention will be shown below.

| Prescription Example 1 (tablet weighing 500 mg each) | |
|---|---|
| 2-methyl-3-piperidino-β-propionaphthone hydrochloride | 250 mg |
| Lactose | 190 mg |
| Crystalline cellulose | 50 mg |
| Magnesium stearate | 10 mg |
| Prescription Example 2 (capsule with 210 mg of filler) | |
| 2,3′,4′-trimethyl-3-piperidinopropiophenone hydrochloride | 10 mg |
| Magnesium stearate | 5 mg |
| Lactose | 135 mg |
| Potato starch | 50 mg |
| Talc | 10 mg |
| Prescription Example 3 (injection ampule with 1 ml capacity) | |
| 2-methyl-3-dimethylamino-β-propionaphthone hydrochloride | 1.0% (by weight) |
| Solubilizer (used, if desired) | proper amount |
| Sodium chloride | ″ |
| Distilled water for injection | ″ |
| Total | 1 ml |
| Prescription Example 4 (ointment of 101 g in total weight) | |
| 2-methyl-3-pyrrolidino-β-propionaphthone hydrochloride | 1 g |
| Emulsified wax | 30 g |
| White vaseline | 50 g |
| Liquid paraffin | 20 g |
| Prescription Example 5 (suppository of 2 g in total weight) | |
| 3′,4′-dimethoxy-2-methyl-3-piperidinopropiophenone hydrochloride | 10 mg |
| Cacao butter | 1990 mg |
| Prescription Example 6 (aerosol) | |
| 2-methyl-3-morpholino-β-propionaphthone hydrochloride | 5.0% (by weight) |
| Sorbitan trioleate | proper amount |
| Dichlorodifluoromethane | ″ |
| Trichlorofluoromethane | ″ |
| Total | 100% (by weight) |

What is claimed:

1. An anti-allergic composition containing a pharmacologically acceptable carrier and a pharmacologically effective amount of a compound of the general formula:

in which:
R₁ is methyl;
A is β-naphthyl; β-naphthyl substituted by halogen, hydroxy, or alkyl having one to four carbon atoms;
B is dialkylamino having each one to four carbon atoms;
pyrrolidino;
morpholino;
piperidino; piperidino substituted by alkyl having one to four carbon atoms or benzyl;
or a pharmacologically acceptable salt thereof.

2. A composition of claim 1 wherein said compound is 2-methyl-3-piperidino-β-propionaphthone.

3. A composition of claim 1 wherein said compound is 2-methyl-3-dimethylamino-β-propionaphthone.

4. A composition of claim 1 wherein said compound is 2-methyl-3-morpholino-β-propionaphthone.

5. A composition of claim 1 wherein said compound is 2-methyl-3-pyrrolidino-β-propionaphthone.

6. A composition of claim 1 wherein said compound is 2-methyl-3-(4-benzyl piperidino)-β-propionaphthone.

7. A composition of claim 1 wherein said compound is 2-methyl-3-(2-methyl piperidino)-β-propionaphthone.

8. A composition of claim 1 wherein said compound is 2-methyl-3-(3-methyl-piperidino)-β-propionaphthone.

9. A composition of claim 1 wherein said compound is 2-methyl-3-(4-methyl-piperidino)-β-propionaphthone.

10. An anti-allergic composition containing a pharmacologically acceptable carrier and a pharmacologically effective amount of 2,6'-dimethyl-3-piperidino-2'-propionaphthone or a pharmacologically acceptable salt thereof.

11. An anti-allergic composition containing a pharmacologically acceptable carrier and a pharmacologically effective amount of 6'-methoxy-2-methyl-3-(4-methyl piperidino)-2'-propionaphthone or a pharmacologically acceptable salt thereof.

12. An anti-allergic composition containing a pharmacologically acceptable carrier and a pharmacologically effective amount of 6'-hydroxy-2-methyl-3-piperidino-2'-propionaphthone or a pharmacologically acceptable salt thereof.

13. An anti-allergic composition containing a pharmacologically acceptable carrier and a pharmacologically effective amount of 6'-chloro-2-methyl-3-piperidino-2'-propionaphthone or a pharmacologically acceptable salt thereof.

14. An anti-allergic composition containing a pharmacologically acceptable carrier and a pharmacologically effective amount of 1'-hydroxy-2-methyl-3-piperidino-2'-proprionaphthone or a pharmacologically acceptable salt thereof.

15. An anti-allergic composition containing a pharmacologically acceptable carrier and a pharmacologically effective amount of a compound of the general formula:

in which:
R₁ is methyl;
A is β-naphthyl substituted by halogen, hydroxy, or alkyl having one to four carbon atoms;
B is dialkylamino having each one to four carbon atoms;
pyrrolidino;
morpholino;
piperidino; piperidino substituted by alkyl having one to four carbon atoms or benzyl;
or a pharmacologically acceptable salt thereof.

* * * * *

UNITED STATES PATENT OFFICE
CERTIFICATE OF CORRECTION

Patent No. 4,563,454          Dated  Jan. 7, 1986

Inventor(s) Akihide Kohda and Teikichi Kurosaki

It is certified that error appears in the above-identified patent and that said Letters Patent are hereby corrected as shown below:

Claim 14, Page 22, Line 6, for "proprionaphtone", read propionaphthone.

Signed and Sealed this

Twenty-second Day of April 1986

[SEAL]

Attest:

DONALD J. QUIGG

Attesting Officer      Commissioner of Patents and Trademarks